United States Patent [19]

Marlett

[11] Patent Number: 4,855,120

[45] Date of Patent: Aug. 8, 1989

[54] PRODUCTION OF SILANE AND USEFUL COPRODUCTS

[75] Inventor: Everett M. Marlett, Baton Rouge, La.

[73] Assignee: Ethyl Corporation, Richmond, Va.

[21] Appl. No.: 261,695

[22] Filed: Oct. 24, 1988

[51] Int. Cl.[4] .............................................. C01B 33/04
[52] U.S. Cl. .................................... 423/347; 556/181; 556/182
[58] Field of Search ................. 556/181, 182; 423/347

[56] References Cited

U.S. PATENT DOCUMENTS

| | | |
|---|---|---|
| 4,016,188 | 4/1977 | Kotzsch et al. ..................... 423/347 |
| 4,474,743 | 10/1984 | Marlett ................................ 423/347 |
| 4,632,816 | 12/1986 | Marlett ................................ 423/347 |
| 4,757,154 | 7/1988 | Marlett et al. ...................... 423/347 |
| 4,778,668 | 10/1988 | Marlett et al. ...................... 423/347 |

Primary Examiner—John Doll
Assistant Examiner—Lori S. Freeman
Attorney, Agent, or Firm—John F. Sieberth

[57] ABSTRACT

A process is described by which two useful products, silane and hydrocarbyloxyaluminun hydride, can be produced concurrently and in excellent yield. The process involves reaction between tetrahydrocarbyloxysilane such as $Si(OEt)_4$ and tertiary amine alane such as $AlH_3 \cdot NEt_3$.

15 Claims, No Drawings

PRODUCTION OF SILANE AND USEFUL COPRODUCTS

TECHNICAL FIELD

This invention relates to the synthesis of silane (SiH4) along with certain useful coproducts, viz., hydrocarbyloxyaluminum hydrides, such as alkoxyaluminum hydrides and aryloxyaluminum hydrides.

BACKGROUND

Silane is employed in the production of polysilicon, which in turn is used in the manufacture of monocrystalline silicon for use in semiconductor devices.

Alkoxyaluminum hydrides are known to be useful as reducing agents in a variety of chemical reactions. See for example: Belgium 615,566 (1962); U.K. 938,043 (1963); U.K. 938,044 (1963); U.S. Pat. No. 3,281,443 (1966); Cooke et al, *J. Org. Chem.*, 1968, 33, 1132–6; U.S. Pat. No. 3,524,870 (1970); Zajac, Jr., et al, *J. Org. Chem.*, 1973, 38, 384–7.

Alkoxyaluminum hydrides have generally been produced in the past by reacting alcohols or aluminum alkoxides with alane in ethereal reaction media. In many cases the alkoxyaluminum hydride product forms a stable complex with the ether and thus is not formed in free (i.e., uncomplexed) form.

U.S. Pat. No. 4,632,816 and U.S. Pat. No. 4,778,668 describe processes for co-producing silane with certain useful co-products.

THE INVENTION

This invention relates to a novel process in which two useful products—silane and hydrocarbyloxyaluminum hydride—can be produced concurrently and in excellent yield. The process is easy to conduct and, when carried out in accordance with preferred embodiments described hereinafter, automatically separates the products into readily recoverable forms.

In accordance with this invention, reaction between tetrahydrocarbyloxysilane and tertiary amine alane forms silane and hydrocarbyloxyaluminum hydride as co-products. Although the reaction may be conducted in bulk (i.e., without a solvent), it is preferred to conduct the process in an inert liquid reaction medium, most preferably in an aromatic hydrocarbon that is in the liquid state under the reaction conditions employed.

Pursuant to a preferred embodiment, there is provided a process which comprises reacting tetrahydrocarbyloxysilane and tertiary amine alane in an inert liquid reaction medium such that silane and hydrocarbyloxyaluminum hydride are co-produced, the reaction being conducted in an inert liquid reaction medium from which silane emerges in the gaseous state and from which the hydrocarbyloxyaluminum hydride emerges as a solid phase. For example, when a tetraalkoxysilane with one or two carbon atoms in each alkoxy group or a tetraaryloxysilane is used in the process and the liquid reaction medium is composed predominantly or entirely of one or more liquid aromatic hydrocarbons such as toluene, silane leaves the liquid reaction medium as a gas and the alkoxyaluminum hydride or aryloxyaluminum hydride co-product emerges from the liquid reaction medium as a solid precipitate. Thus the preferred liquid reaction media not only enhance reaction rate and facilitate the reaction, but additionally automatically separate the coproducts into readily recoverable uncomplexed forms.

Tetrahydrocarbyloxysilanes which may be used in the process may be represented by the formula $(RO)_4Si$, wherein each R is, independently, a hydrocarbyl group such as alkyl, cycloalkyl, aryl, aralkyl, and the like. Each such group may contain up to about 12 or more carbon atoms but preferably contains up to 6 carbon atoms. The hydrocarbyl groups may differ from each other, but preferably are identical to each other. The hydrocarbyl groups may contain inert substituents such as alkoxy, cycloalkoxy, aryloxy, hydrocarbylsilyl, hydrocarbylsiloxy, alkoxysilyl, alkoxysilyloxy, and the like.

Typical tetrahydrocarbyloxysilanes that may be used in the process include tetramethoxysilane, tetraethoxysilane, tetrapropoxysilane, tetraisopropoxysilane, tetrabutoxysilane, tetradecoxysilane, triethoxymethoxysilane, dibutoxydiethoxysilane, tetracyclopentoxysilane, tetra(methylcyclopentoxy)silane, tetracyclohexylcarbinyloxysilane, tetraphenoxysilane, methoxytritolyloxysilane, tetrabenzyloxysilane, and the like.

Any tertiary amine alane can be used that is co-reactive with a tetrahydrocarbyloxysilane to co-produce silane and hydrocarbyloxyaluminum hydride. The tertiary amine portion of the complex may thus be aromatic, heterocyclic, aliphatic or cycloaliphatic. Preferred are the trialkylamine alane complexes such as trimethylamine alane, bis(trimethylamine) alane, triethylamine alane, tripropylamine alane, tributylamine alane, and like straight and branched chain trialkylamine alane complexes wherein each alkyl group which may contain up to about 12 carbon atoms but which preferably contains from 1 to 6 carbon atoms. However, compounds in which one to two equivalents of alane is/are complexed with a tertiary diamine such as the triethylenediamine alane and N,N,N',N'-tetramethylethylenediamine alane complexes may be employed.

Other examples of tertiary amine alanes that may be used in the process include tricyclohexylamine alane, N,N-dimethylethylamine alane, N,N-diethylmethylamine alane, N-methylmorpholine alane, quinuclidine alane, and the like.

Suitable reaction media include dialkyl ethers, cyclic ethers, tertiary amines, paraffinic hydrocarbons, cycloparaffinic hydrocarbons, aromatic hydrocarbons, tertiary (alkoxyalkyl) amines, and like materials (including mixtures of two or more such materials) which are in the liquid state under the reaction conditions selected for use. As noted above use of reaction media composed predominantly (more than 50% by weight) or entirely of one or a mixture of liquid aromatic hydrocarbons such as toluene, o-xylene, m-xylene, p-xylene, ethylbenzene, trimethylbenzenes, 1,2-diethylbenzene, 1,3-diethylbenzene, 1,4-diethylbenzene, 3,5-diethyltoluene, n-butylbenzene, 3-propyltoluene, 4-propyltoluene, tetrahydronaphthalene, 1,2,3,4-tetramethylbenzene, 1,2,3,5-tetramethylbenzene, and the like, including mixtures of two or more such materials, are preferred. Mixtures of two or more different types of solvents, such as a mixture of paraffinic and aromatic hydrocarbons, a mixture of one or more hydrocarbons with one or more tertiary amines, etc., may also be used.

Reaction temperatures in the range of about 0° to about 120° C. are generally satisfactory, although even higher or lower temperatures may be used in situations which warrant or justify use of such temperatures. Ordinarily it is preferred to conduct the reaction at a temperature in the range of about 10° to about 60° C.

The process may be conducted at elevated or reduced pressures if desired. However it is ordinarily carried out at atmospheric pressures.

When employing tetraalkoxysilanes and 1:1 molecular trialkylamine alane complexes as reactants, the reaction may be depicted by the following equation:

$$Si(OAlk)_4 + 2AlH_3 \cdot NR_3 \rightarrow SiH_4 + 2(AlkO)_2AlH + 2R_3N$$

With tetraaryloxysilanes and 1:1 molecular trialkylamine alane complexes as reactants, the reaction tends to proceed in accordance with the following equation:

$$3Si(OAr)_4 + 8AlH_3 \cdot NR_3 \rightarrow 3SiH_4 + 4(ArO)_2AlH \cdot ArOAlH_2 + 8R_3N$$

The reactants are normally used for convenience in approximately stoichiometric proportions. However the proportions used are not critical since the reaction tends to be little affected by changes in proportions. Thus as between the reactants, the reactant present in the lower proportion relative to the stoichiometry of the particular reaction being conducted, becomes the limiting reactant.

Having described the basic concepts of this invention, reference will now be made to the following specific examples which are illustrative but not limitive of its practice.

EXAMPLE 1

Reaction of Si(OEt)$_4$ with AlH$_3$·NEt$_3$

The amine alane was prepared by mixing 0.92 g (6.7 mmole) AlCl$_3$ with 3.05 g (30 mmole) Et$_3$N in 25 g toluene. When the AlCl$_3$ had disappeared 1.40 g (25 mmole) NaAlH$_4$ was added and the resulting mixture stirred in a closed flask under N$_2$ at room temperature for 4 hours. The final slurry was filtered and the filtrate (25.1 g) analyzed (found: 0.31% H; 2.87% Al; <0.001% Cl). To a 50 mL round bottom 3-neck flask was added 13.5 g (14 mmole AlH$_3$) of this solution, which was then connected to the gas collection train and swept with prepurified H$_2$. To a 25 mL transfer funnel was added a mixture containing 2.10 g (10 mmole) Si(OEt)$_4$ and 4.40 g toluene. The funnel was attached to the flask and the contents added dropwise to the stirred hydride solution over a 30-minute period at 35° C. The silane produced was condensed at −196° C. After another 30 minutes the trap was isolated, evacuated and the liquid N$_2$ removed, allowing the SiH$_4$ to expand into the calibrated section. The moles of gas produced (7.0 mmole) was calculated using the Ideal Gas Law. A sample of the gas was then collected and analyzed by GC/MS. These determinations indicated that the silane was of high purity and formed in a yield of almost 70 percent.

EXAMPLE 2

Reaction of Si(OEt)$_4$ with AlH$_3$·NEtMe$_2$

The procedure of Example 1 was repeated with the exception that an equivalent amount of Me$_2$EtN was used in place of the Et$_3$N. The silane yield was 76 percent and it had even higher purity than the silane produced in Example 1.

EXAMPLE 3

Reaction of Si(OEt)$_4$ with AlH$_3$·NEt$_3$

The procedure of Example 1 was again repeated, but in this instance using a reaction temperature of 55° C. The yield of silane was 74 percent. Solvent was stripped at 60° C. in vacuo from the solid product formed in the reaction to give a white powder. Analysis of this powder gave values very close to the composition (EtO)$_2$AlH. (Theory: Active H, 0.85%; Al, 22.9%. Found: Active H, 0.81%; Al, 22.6%.) The X-ray powder diffraction powder pattern

| d, Å | I/I$_o$ |
|------|---------|
| 7.71 | 100 |
| 6.69 | 65 |
| 4.02 | 18 |
| 3.82 | 46 | satisfactorily matched the pattern reported heretofore for product made by reaction of AlH$_3$ with ethanol in diethyl ether.

To prove the stoichiometry of the reaction the following procedure was used: To a 50 mL round bottom flask was added 0.68 g AlCl$_3$ (5.0 mmole); 12.0 g dry toluene; 2.05 g Et$_3$N (20 mmole). Then, when the AlCl$_3$ dissolved and the mixture cooled, 2.16 g NaAlH$_4$ (15 mmole+5% excess) was added. The flask was stoppered and magnetically stirred for 4 hours at RT. The white slurry was filtered through a coarse glass frit. Wt. filtrate=14.55 g.

To a 25 mL transfer funnel were added 2.10 g Si(OEt)$_4$ (10 mmole), and 3.0 g dry toluene. The funnel and 50 ml 3-neck round bottom flask containing the filtrate were attached to the gas collection train, and swept with purified H$_2$. The condenser was cooled with dry ice/acetone and the trap immersed in liquid N$_2$. A purge of H$_2$ was maintained through the system, fed at the top of the funnel. A 35° C. water bath was placed under the reactor.

While agitating the amine alane solution, the Si(OEt)$_4$/toluene solution was added dropwise over a 15-minute period. A white, gelatinous slurry slowly formed, but stirred well. The system was swept with H$_2$ for another 30 minutes, then the valve between condenser and calibrated section closed and the trap pumped down to <1 mm Hg. This section was isolated and the liquid N$_2$ removed, allowing the SiH$_4$ in the trap to vaporize. The gas produced, calculated by the Ideal Gas Law, amounted to 9.3 mmole. The yield of silane was 93 percent.

The foregoing results show that the stoichiometry for this reaction is:

$$Si(OEt)_4 + 2AlH_3 \cdot NEt_3 \rightarrow SiH_4 + 2(EtO)_2AlH + 2Et_3N$$

EXAMPLE 4

Reaction of Si(OPh)$_4$ with AlH$_3$·NEt$_3$

The amine alane was prepared by mixing 0.44 g (3.3 mmole) AlCl$_3$ with 1.34 g (13.3 mmole) Et$_3$N in 11 g toluene. When the AlCl$_3$ had disappeared 0.58 g (10.5 mmole) NaAlH$_4$ was added and the resulting mixture stirred in a closed flask under N$_2$ at room temperature for 4 hours. The final slurry was filtered and the filtrate placed in a 50 mL round bottom 3-neck flask, which was then connected to the gas collection train and swept with prepurified $H_2$. To a 25 mL transfer funnel was added a mixture containing 3.61 g (9.0 mmole) Si(OPh)$_4$ and 9.0 g toluene. The funnel was attached to the flask and the contents added dropwise to the stirred hydride solution over a 30-minute period at 35° C. At this time an additional 13.8 g dry toluene was added to the reaction mixture which had become very thick. The reaction continued an additional hour. At the end of this period, the silane produced and condensed at $-196°$ C. was expanded into the calibrated section. The moles of gas produced (4.8 mmole) was calculated using the Ideal Gas Law. The silane yield was 48 percent.

What is claimed is:

1. A process which comprises reacting tetrahydrocarbyloxysilane and tertiary amine alane such that silane and hydrocarbyloxyaluminum hydride are co-produced.

2. A process of claim 1 conducted in an inert liquid reaction medium.

3. A process of claim 1 conducted in a liquid aromatic hydrocarbon reaction medium.

4. A process of claim 1 in which the tetrahydrocarbyloxysilane used is a tetraalkoxysilane.

5. A process of claim 1 in which the tetrahydrocarbyloxysilane used is a tetraaryloxysilane.

6. A process of claim 1 wherein the tertiary amine alane is a trialkylamine alane in which each alkyl group has up to 6 carbon atoms.

7. A process which comprises reacting tetrahydrocarbyloxysilane and tertiary amine alane in an inert liquid reaction medium such that silane and hydrocarbyloxyaluminum hydride are co-produced, the reaction being conducted in an inert liquid reaction medium from which silane emerges in the gaseous state and from which the hydrocarbyloxyaluminum hydride emerges as a solid phase.

8. A process of claim 7 in which the tetrahydrocarbyloxysilane used is a tetraalkoxysilane.

9. A process of claim 7 in which the tetrahydrocarbyloxysilane used is a tetraaryloxysilane.

10. A process of claim 7 wherein the liquid reaction medium is composed predominantly or entirely of one or more aromatic hydrocarbons.

11. A process of claim 7 wherein the tetrahydrocarbyloxysilane is a tetraalkoxysilane having one or two carbon atoms in each alkoxy group.

12. A process of claim 7 wherein the tetrahydrocarbyloxysilane is a tetraalkoxysilane having one or two carbon atoms in each alkoxy group and the liquid reaction medium is composed predominantly or entirely of toluene.

13. A process of claim 7 wherein the tertiary amine alane used is a trialkylamine alane in which each alkyl group has up to 6 carbon atoms.

14. A process of claim 7 wherein the tertiary amine alane used is triethylamine alane or diethylmethylamine alane.

15. A process of claim 7 in which the tetrahydrocarbyloxysilane used is a tetraalkoxysilane and the tertiary amine alane used is a trialkylamine alane in which each alkyl group has up to 6 carbon atoms.

* * * * *